(12) United States Patent
Hubert et al.

(10) Patent No.: US 10,390,971 B2
(45) Date of Patent: Aug. 27, 2019

(54) CYLINDER HEAD, ELEMENT AND FLANGE OF A PISTON ENGINE

(71) Applicant: MECACHROME FRANCE, Amboise (FR)

(72) Inventors: Pierre-Julien Hubert, Igny (FR); Jean-Pierre Boudy, Bievres (FR); Sébastien Vermeiren, Versailles (FR)

(73) Assignee: MECACHROME FRANCE, Amboise (FR)

( * ) Notice: Subject to any disclaimer, the term of this patent is extended or adjusted under 35 U.S.C. 154(b) by 28 days.

(21) Appl. No.: 15/324,479

(22) PCT Filed: Jul. 9, 2015

(86) PCT No.: PCT/FR2015/051900
§ 371 (c)(1),
(2) Date: Jan. 6, 2017

(87) PCT Pub. No.: WO2016/005704
PCT Pub. Date: Jan. 14, 2016

(65) Prior Publication Data
US 2017/0156891 A1 Jun. 8, 2017

(30) Foreign Application Priority Data
Jul. 9, 2014 (FR) .................... 14 56618

(51) Int. Cl.
*A61F 2/46* (2006.01)
*F02F 1/38* (2006.01)
*F02F 1/24* (2006.01)

(52) U.S. Cl.
CPC .............. *A61F 2/4657* (2013.01); *F02F 1/38* (2013.01); *F02F 1/242* (2013.01); *F02F 2001/249* (2013.01)

(58) Field of Classification Search
CPC ...... A61F 2/4657; F02F 1/38; F02F 2001/249
(Continued)

(56) References Cited

U.S. PATENT DOCUMENTS

| 1,479,129 A | 1/1924 | Feilner |
| 4,018,195 A | 4/1977 | Bandrowski, Jr. |

(Continued)

FOREIGN PATENT DOCUMENTS

| DE | 2514592 A1 | 10/1976 |
| WO | 03/062621 A1 | 7/2003 |

OTHER PUBLICATIONS

Written Opinion of the International Searching Authority dated Nov. 5 2015, issued in corresponding International Application No. PCT/FR2015/051900, filed Jul. 9, 2015, 7 pages.
(Continued)

*Primary Examiner* — Syed O Hasan
(74) *Attorney, Agent, or Firm* — Christensen O'Connor Johnson Kindness PLLC (57) ABSTRACT

A cylinder head, an element and a base plate of a longitudinal piston engine having a cylinder head body and a base plate comprising at least one element, the base plate being interposed between a combustion chamber and the cylinder head body, comprising an upper face facing the cylinder head body and an opposing lower face arranged to face the combustion chamber and being attached to the cylinder head body, the cylinder head body being made from a material with a mass density and hardness that are less than those of the material constituting the base plate. The base plate and the body are assembled by screws for fastening the base plate to the cylinder head that are located towards the periphery of the base plate and of the body and by at least one part for fastening the cylinder head to the base plate including a threaded end designed to be engaged in a
(Continued)

corresponding orifice of the base plate, said orifice being located closer to the center of the base plate than the fastening screws.

16 Claims, 5 Drawing Sheets

(58) Field of Classification Search
USPC .............................. 123/41.76, 193.5, 193.3
See application file for complete search history.

(56) References Cited

U.S. PATENT DOCUMENTS

| | | | |
|---|---|---|---|
| 4,034,723 A * | 7/1977 | Hamparian | ............. F02B 77/02 123/193.5 |
| 4,106,444 A * | 8/1978 | Deutschmann | ......... F02F 1/166 123/193.5 |
| 4,112,906 A | 9/1978 | Spencer | |
| 2005/0061286 A1 * | 3/2005 | Molina | ..................... F02F 1/24 123/193.3 |

OTHER PUBLICATIONS

International Preliminary Report on Patentability dated Jan. 10, 2017, issued in corresponding International Application No. PCT/FR2015/051900, filed Jul. 9, 2015, 1 page.
International Search Report dated Nov. 5 2015, issued in corresponding International Application No. PCT/FR2015/051900, filed Jul. 9, 2015, 3 pages.
Written Opinion of the International Searching Authority dated Nov. 5 2015, issued in corresponding International Application No. PCT/FR2015/051900, filed Jul. 9, 2015, 6 pages.

* cited by examiner

CYLINDER HEAD, ELEMENT AND FLANGE OF A PISTON ENGINE

BACKGROUND

Embodiments of the present disclosure relate to a longitudinal piston-engine cylinder head having a cylinder head body and a base plate comprising at least one element, the base plate being interposed between a combustion chamber and the cylinder head body, comprising an upper face facing the cylinder head body and an opposing lower face arranged to face the combustion chamber and attached to the cylinder head body.

It also relates to a base plate, a base plate element and an assembly including a piston-motor cylinder head with such a base plate.

It also relates to a method for assembling a cylinder head body with such a base plate by screwing.

It can be used particularly, but not necessarily exclusively, in the domain of compact engines having reduced mass, high power density (ratio between the mechanical power supplied by the engine and the total volume corresponding to the maximum swept volume of the piston), and very high thermodynamic efficiency, in particular for an aircraft or a racing car.

Improving the efficiency of the thermodynamic cycle of a piston engine, regardless of the cycle chosen (Carnot, Stirling, diesel, etc.), is an ongoing concern for engine manufacturers.

Engine efficiency depends on compression and the energy intake in the combustion chamber, and more specifically the maximum respective temperature and pressure values that can be reached therein.

It is known to increase pressure by supercharging the combustion chamber with oxidant (air).

Nonetheless, this technique involves a compromise between pressure inside the chamber and engine weight.

Indeed, to achieve high pressures and the combustion temperature of the fuel, materials that can mechanically withstand these pressure and temperature conditions need to be used and/or the dimensions of the parts need to be adapted to the material chosen.

This type of material, such as steel or cast iron, is heavy (mass density greater than 5000 kg/m$^3$).

To overcome this drawback, an engine including an engine block made of a strong material and a cylinder head made of a lighter material has been proposed.

However, in this case, the cylinder head has a side facing the combustion chamber that is made of relatively weak materials, which limits the potential of the engine.

A cylinder head made of two parts of different materials that are welded together is also known (EP 0262240).

Such a cylinder head nonetheless has drawbacks.

Indeed, such a cylinder head cannot operate in high pressure and temperature ranges, in particular if the thickness of the base plate is reduced in order to limit weight.

Such a cylinder head is not simple or reversible to assemble and requires the two parts of different materials to be welded together, which is also complex and costly.

Finally, the parts must be perfectly shaped since the slightest dimensional defect would result in a significant loss of efficiency.

A device made of two different materials but that has low resistance to vibration and uses an adhesive layer between the materials is also known (WO 03/062621).

Document DE 2514592 describes a two-part single-cylinder cylinder head with a cooling chamber that is liable to corrosion problems.

SUMMARY

Embodiments of the present disclosure are intended to overcome these drawbacks and to provide a cylinder head, a base plate and an element that satisfies the related practical requirements better than in the prior art, in particular by enabling improved engine efficiency compared to the prior art without compromising the related weight requirements.

Accordingly, the present disclosure enables high pressures to be achieved in the combustion chamber (cylinder pressure) using a cylinder head body made of light alloy for example, or for the weight of a cylinder head made of a heavy alloy to be reduced for a given maximum compression pressure.

Indeed, the disclosure enables pressures exceeding 250 bars or even 300 bars and temperatures exceeding 250° C. to be achieved, bearing in mind that cylinder heads in the prior art conventionally operate at pressures between 180 bars and 200 bars and combustion chamber temperatures of less than 200° C., hence the excellent efficiency observed.

The disclosure also makes assembly of the cylinder head on the engine simpler, quicker and cheaper. The disclosure also enables assembly that improves the flatness of the lower face of the base plate or of the base plate elements between one another.

Finally, the disclosure also enables elements of the cylinder head to be replaced and/or recycled.

For this purpose, the disclosure notably proposes a longitudinal piston-engine cylinder head having a cylinder head body and a base plate comprising at least one element, the base plate being interposed between a combustion chamber and the cylinder head body, comprising an upper face facing the cylinder head body and an opposing lower face arranged to face the combustion chamber and attached to the cylinder head body, the cylinder head body being made of a material with mass density and hardness values that are lower than the mass density and hardness values of the material used to make the base plate, characterized in that the base plate and the body are assembled with screws used to fasten the base plate to the cylinder head that are located towards the periphery of the base plate and of the body and at least one part used to fasten the cylinder head to the base plate having a threaded end engaged in a corresponding orifice of the base plate, the orifice being located closer to the center of the base plate than the fastening screws.

Hardness means the resistance provided by a surface of a sample of material to penetration of a punch, such as a hardened steel ball (Brinell hardness according to the standard EN ISO 6506 revised in 2005) or a diamond pyramid (Vickers hardness according to the standard EN ISO 6507 revised in 2005).

In an advantageous embodiment, the criteria of hardness is replaced by endurance limit.

Endurance limit $\sigma_D(N)$ means the fatigue limit for a given load type (advantageously traction, but also flexion and torsion) and for a mean stress $\sigma_m$ as defined in the standard NF A 03-400 (updated in August 1983) for a number of load cycles N (for example 10$^6$) applied to a test piece of a given shape (for example cylindrical section with a diameter of 3 mm and a length of 1 cm) and a given surface state, at a temperature and/or within a given temperature range (for example between 100° C. and 400° C., for example 350° C.).

The measurement is taken by loading the test piece until the end-of-test criteria is satisfied (completion of the number of cycles or rupture of test piece).

Since the endurance limit value towards which the stress amplitude tends after N cycles depends on the shape of the test piece and the temperature, endurance limit comparisons between materials must naturally be made under the same test-piece and temperature conditions.

In general, the endurance limit is written $\sigma_D(N)=\sigma_m \pm \sigma_m$ where $\sigma_a$ is the stress amplitude corresponding to the endurance limit for a specific mean stress value $\sigma_m$.

Center means the isobarycenter of the lower face of the base plate.

Towards the periphery means, for example, the zone of the base plate extending from the outer edges of same to a homothetic line of the edge located a few millimeters away from same, for example 1-2 cm.

Screw fastening may be understood by the person skilled in the art to cause fragility, in consideration of the mechanical stresses generated by the engine, thereby resulting in deformation of the base plate (drum skin effect). The disclosure makes it possible to sufficiently limit and/or eliminate such deformations, which adversely affect mechanical strength, by adding at least one clamping point, advantageously centrally or near the middle, to prevent detachment of the base plate or of the base plate element if the base plate is made of several elements, in the central zone, the clamping point being located inside the closed sealing gasket between the cylinder head and the base plate, where applicable.

As shown and in order to ensure the correct assembly of the cylinder head and the base plate elements, same are clamped together using peripheral fastening screws and at least one fastening part positioned more centrally than the screws in order to correctly distribute the contact pressures.

Once assembled on the cylinder head body, the base plate comprising at least one element has a lower face (accessible and on the other side of the assembly) which is machined notably to ensure the flatness of same before final fastening to the engine block.

Indeed, the base plate is sandwiched between the engine block and the cylinder head body and has different supports (cylinder head gasket and upper face of the engine block). This causes the base plate to deform slightly under pressure, in particular inclining the valve seat faces, which has an adverse effect on the efficiency and sealing of the engine.

The assembly method enables correction of the deformation of the base plate during assembly on the engine block, thereby improving geometric conformity when in operation.

After several iterations, for example by trial and error, the tightening force values for the fastening part are established, enabling achievement of a deformation of the base plate, and more specifically of the lower face of same, before machining, that is close to and/or identical to the real deformation of same (when a nominal tightening force is applied to the fastening part once the base plate has been mounted on the engine block), the other fastening elements being tightened to the nominal values of same (fastening screws, nuts, etc.).

The prior deformation thus obtained before machining enables the nominal operational deformation to be anticipated and compensated for, thereby limiting or eliminating residual deformation caused by different tightening operations by machining.

In advantageous embodiments, any of the following arrangements can also be used:

the cylinder head body is made of a material that has higher thermal conductivity than the material used to make the base plate, the cylinder head body is made of aluminum, aluminum alloy, magnesium or magnesium alloy, and the base plate is made of steel or nickel alloy, the orifice is located within or substantially within a longitudinal plane centered on and orthogonal to the base plate. Located substantially means about the central longitudinal line (of symmetry) of the cylinder head, for example at a distance of less than ±5 cm from the line, the base plate comprises at least two identical juxtaposed coplanar elements, each having four fastening screws (for example at each corner) and one orifice. A different number of periphery screws for each element may also be used, the orifice is centered in relation to the base plate and/or the base plate element, the orifice passes entirely through the base plate, the fastening part includes a bushing arranged to individually receive a first functional device used in operation of the engine and that is required to interact with the combustion chamber. This provides the assembly with excellent axial rigidity, while enabling access via the bushing to the inside of the combustion chamber, the fastening part or parts for the cylinder head pass through the through-holes in the body, bear against the body and are screwed into the base plate, and the fastening screws for the base plate bear against the base plate and are screwed into the body, the tightening force of the fastening part or parts is at least twice as great as the tightening force of the fastening screws for the base plate, for example three times as great, and advantageously four times as great, the base plate extending entirely within a plane includes an internal cooling circuit to circulate a heat-transfer fluid, the circuit having at least one fluid inlet, a fluid circulation channel in the thickness of same and several fluid drainage channels in the body of the cylinder head, the ducts forming an angle greater than 20° in relation to the plane of the base plate passing around the gas exhaust ducts of the body of the cylinder head.

In this document, channel means a duct flush with a face of the base plate and therefore open on the face, for example like a channel formed by machining the upper face of the base plate. Channel also means an internal duct entirely contained within the thickness of the base plate, i.e., with reference to the previous example, the upper face is closed and possibly flat, such as a base plate being obtained for example by casting.

This arrangement enables rapid local cooling with very little water (half a liter of water compared to 2-3 liters of water with a traditional cylinder head).

The water rises from the block, enters the base plate before cooling the cylinder head body using the drainage ducts forming cooling curtains about the extremely hot exhaust conduits, the channel, extending along a path, has an average width 1 that is less than 20% of the transverse dimension or width of the base plate and includes, along the path, at least one narrowing extending over at least 2.5% of the length of the path and the average width of the narrowing parallel to the plane of the base plate is less than 10% of the width of the base plate. The narrowing enables acceleration of the coolant fluid where greatest cooling performance is required.

The transverse dimension is the dimension perpendicular to the longitudinal direction of the base plate, the circuit inside the base plate has holes between the valve seats. This arrangement makes it possible to cool the portions between the valve seats, which are consistently difficult to reach, the base plate has at least one valve seat that is integral with the base plate. Consequently, the valve seats may be attached or otherwise. The seat may therefore be made of a more specific material and/or be replaced, which obviates the need to replace the entire base plate or element, the cylinder head has at least one sealing gasket between the body and the base plate, since the cylinder head body includes admission and exhaust conduits, the exhaust conduits are provided with a sleeve made of a material having very low thermal conductivity, the sleeve being held in position in relation to the exhaust conduit by end portions, beside which there is a space between the sleeve and the facing portion of the exhaust conduit, in order to limit heat exchanges.

More specifically, very low thermal conductivity in this case means a thermal conductivity p of less than 70 $W.m^{-1}.K^{-1}$, for example less than 40 $W.m^{-1}.K^{-1}$, for example 20 $W.m^{-1}.K^{-1}$, which is the thermal conductivity of titanium, the base plate includes an opening for a second functional device used in operation of the engine and that is required to interact with the combustion chamber.

The second device may be of any type and may be contained within the bushing or otherwise, enabling a good geometric fit.

The disclosure also proposes an element of a base plate for a cylinder head of a piston engine, the element extending entirely within a plane, having an upper face and an opposing lower face and being designed to be interposed as an interface between a combustion chamber of the engine and a body of the cylinder head, the upper face having an internal cooling circuit to circulate a heat-transfer fluid, characterized in that it is designed to be coplanar with other identical elements of the base plate, and in that it has:

first through-holes for screws for fastening the element to the cylinder head body that are located towards the periphery of the element, and at least one second screw orifice for a part for fastening the cylinder head body to the element that is closer to the center of the base plate than the first fastening orifices.

The disclosure also proposes a base plate for a cylinder head of a piston engine, the base plate extending entirely within a plane including an upper face and an opposing lower face and being designed to be interposed as an interface element between a combustion chamber of the engine and a body of the cylinder head, wherein the upper face has at least one internal cooling circuit to circulate a heat-transfer fluid, and in that it has:

first through-holes for screws for fastening the base plate to the cylinder head body distributed around the entire periphery and along the length of the base plate, and at least one second screw orifice for at least one part for fastening the cylinder head body to the element that is closer to the center of the base plate than the first fastening orifices.

In advantageous embodiments of the base plate or base plate element, the internal cooling circuit is contained within the thickness of the base plate and the upper face is flat or substantially flat. In other advantageous embodiments, the upper face has at least one internal cooling circuit [(open top) channel].

The disclosure also proposes an engine assembly including a cylinder head of the type described above, wherein it includes fuel injectors, spark plugs or ignition devices mounted in the bushings as functional parts.

Ignition device means notably the devices for triggering combustion of fuel/oxidant in a controlled-ignition engine.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Figure 1:
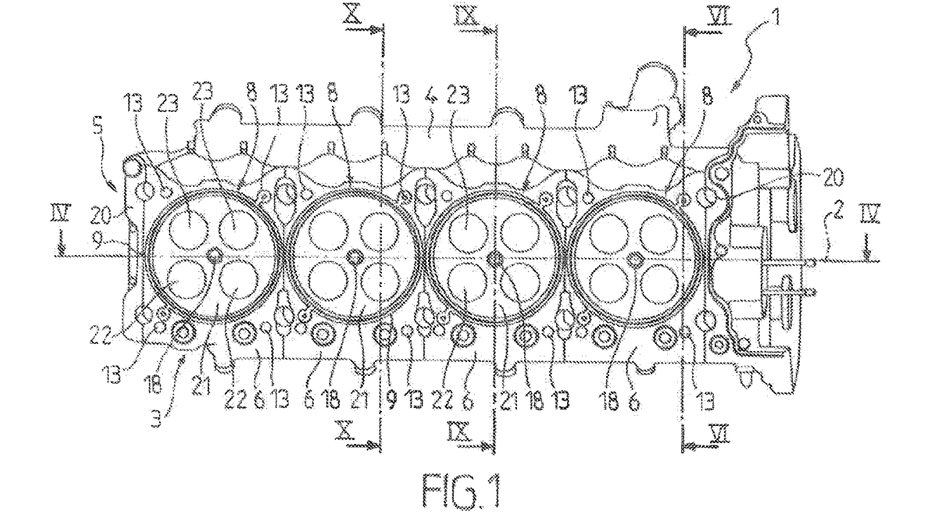
FIG. 1 is a top view of the lower face of a cylinder head according to one embodiment of the disclosure that is designed to be mounted on an engine block.

FIG. 1 is a bottom view of a cylinder head 1 of a piston engine (in this case four pistons) extending longitudinally along an axis 2, seen from the combustion-chamber-side face 3.

The cylinder head comprises a cylinder head body 4 and a base plate 5 formed by four identical elements 6 corresponding to each of the pistons.

Figure 2:
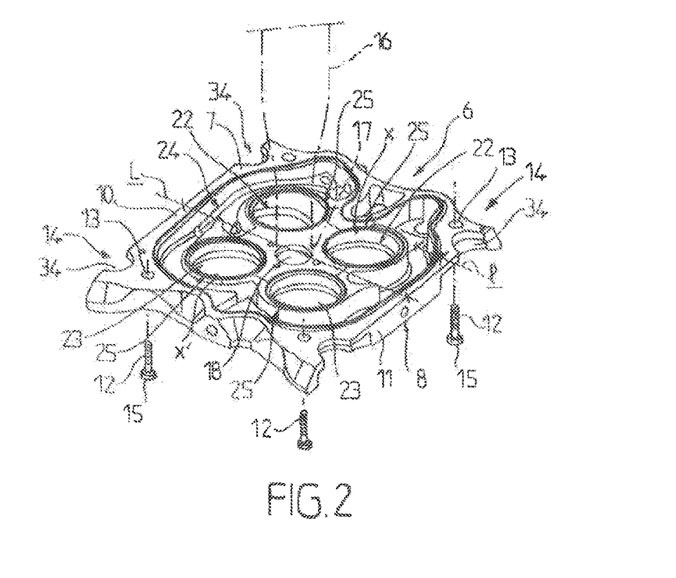
FIG. 2 is a top perspective view of an element of a base plate of the cylinder head in FIG. 1.

Also with reference to FIG. 2, these elements 6 have an upper face 7 designed to face the cylinder head body 4 and a lower face 8, which is for example flat, provided with a circular metal seal 9 facing the upper periphery of each of the four combustion chambers of the related pistons.

The cylinder head body, the base plate and the four elements 6 are all made of metal.

The cylinder head body being made of a first material with a mass density $\rho_1$ and a hardness, for example a Vickers hardness, HV1 and/or a fatigue limit $\sigma_D1(N)$, the base plate and more specifically these four elements 6 have a mass density $\rho_2$ and a hardness HV2 and/or a fatigue limit $\sigma_D2(N)$.

In the embodiment more specifically described here, the cylinder head body is also made of a first material with a thermal conductivity $\lambda_1$, a modulus of elasticity E1 and an elastic limit Re1, the base plate and more specifically these four elements 6 have a thermal conductivity $\lambda_2$, a modulus of elasticity E2 and an elastic limit Re2.

The mass density $\rho_1$ and the hardness HV1 and/or the fatigue limit $\sigma_D1(N)$ are lower, i.e. lower than the mass density $\rho_2$ and the hardness HV2 and/or the fatigue limit $\sigma_D2$ respectively.

In the embodiment more specifically described here, the thermal conductivity $\lambda_1$ of the cylinder head body is greater, i.e. higher than the thermal conductivity $\lambda_2$ of the base plate and the elastic limit Re1 is lower than Re2.

The cylinder head is for example made of aluminum or aluminum alloy and the base plates or the base plate elements are made of steel, for example 316L steel.

According to the embodiment more specifically described here, the base plate elements are generally parallelepipedic plates 10, for example substantially square, in which the periphery 11 is designed and arranged to enable the necessary adaptations to the cylinder head body, the adaptations being related notably to the admission and exhaust orifices and to the studs for fastening the cylinder head to the engine block, in a known manner.

Each of the elements is assembled on the body using four screws 12 for fastening the base plate element to the cylinder head, the screws being arranged towards the periphery 11 of the base plate elements.

More specifically, each screw comprises a flat bearing head, an elongate smooth cylindrical body ending with a threaded portion arranged to pass through to the other side of the base plate when the screw is inserted into a corresponding through-hole 13 in the plate.

The base plate element has four through-holes 13 located at the four corners 14 of the element.

The bearing heads 15 bear against the outer face 8 of the base plate element, for example in the notches in which same are completely engaged so as not to project beyond the plane of the face 3.

The threaded portion of the screws 12 cooperates with the opposing threaded orifices on the lower flat outer face F of the cylinder head body.

Each base plate element is also attached to the cylinder head body by means of a fastening part 16 shown using a mixed line in FIG. 2, passing through the cylinder head body entirely, centered in relation to the corresponding base plate element and including a threaded end 17 designed to engage in a threaded orifice 18, which in this case passes through the base plate, but which may also be blind. The orifice is therefore located at the center or substantially at the center of the base plate in relation to the fastening screw.

End elements 20 located on each side and forming slats of the same thickness as the base plate are provided to achieve identical base plate elements 6, in consideration of the configuration of the lower face F of the cylinder head body. These are also attached to the outer face of the cylinder head body using screws. The end elements 20 provide support and distribute the stresses related to assembly of the cylinder head body on the engine block.

They are therefore the same thickness as the base plate elements 6 of the same shape for the benefit of the zone of the cylinder head body at the longitudinal end of same. They are therefore fastened using fastening screws similar to the ones used for the base plate elements.

With reference to FIG. 1, each base plate element 6 associated with a corresponding combustion chamber (circular disk 21) has four cylindrical through orifices, i.e. two admission orifices 22 and two exhaust orifices 23 associated with the corresponding valves, in a known manner.

Each base plate element and the corresponding portion of the cylinder head body includes an internal cooling circuit. More specifically, the upper face 7 of the element 6 includes a circulation channel 24 in the thickness of same, that extends along a path designed to optimize cooling of the plate, which tends to get very hot on account of the low coefficient $\lambda$ of same. To do so, the average width of the channel 1 is determined, by calculation and in a manner known to the person skilled in the art, to be sufficient but less than 15% of the transverse dimension (or width) L of the base plate.

Such an arrangement ensures that the base plate is not weakened, including in consideration of the pressure conditions applied.

The internal circuit also includes a plurality of narrowings 25 along the path at the hottest points of the plate in order to accelerate the start of cooling at these points.

Advantageously, the total cumulative width of these narrowings is equal to 20% of the length of the path. The width of the narrowings is for example x=3 mm parallel to the plane of the base plate, less than 5% of the width of the base plate.

The dimensions x, x', etc. of these narrowings are calculated by the person skilled in the art in consideration of parameters relating to mechanical stresses, pressure drops and expected temperature in the cylinder head in the absence of any cooling.

In the remainder of the description, the same reference signs are used to identify the same elements.

Figure 3:
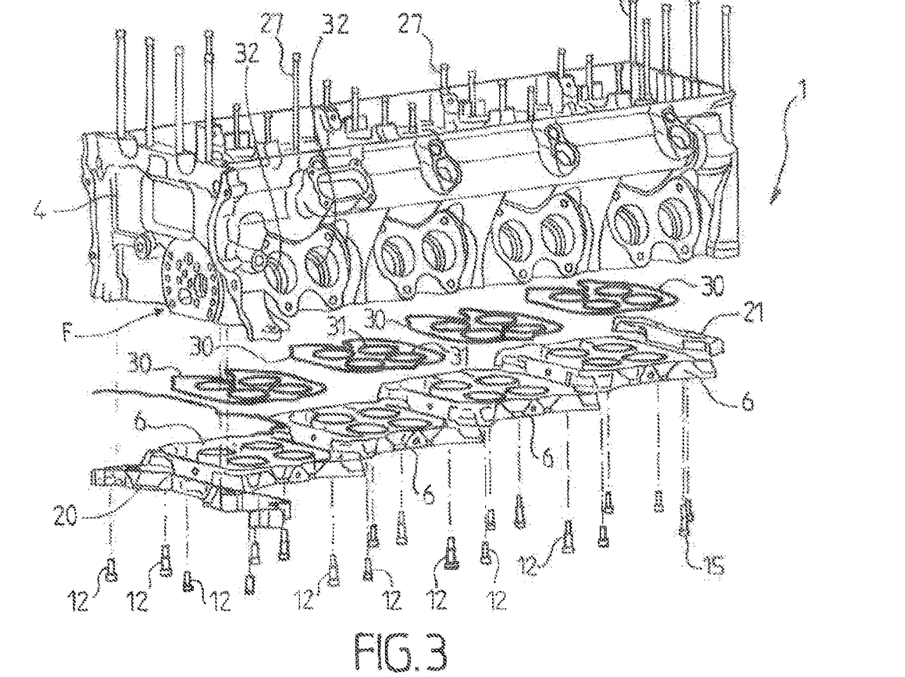
FIG. 3 is an exploded perspective view of a cylinder head according to the embodiment in FIGS. 1 and 2.

FIG. 3 is a perspective view of the cylinder head 1 in FIG. 1. The cylinder head comprises the cylinder head body 4 and the base plate elements 6 of the type described with reference to FIG. 2. These are therefore attached to the cylinder head body by screws 12, as described above, that pass through each element and cooperate with an opposing threaded hole formed in the lower face F of the cylinder head body.

Appropriately shaped O-ring sealing gaskets 30 and 31 are provided on the upper faces 7 of the elements 6 around the periphery of the base plate element, towards the outside in relation to the internal cooling circuit, and around the exhaust and admission openings respectively.

The cylinder head body is for example made of aluminum alloy and is substantially formed in a known manner, with the exception of the cooling circuit, which is more specific and described in greater detail below with reference to FIGS. 7 and 8.

In a known manner, the cylinder head body includes inclined admission conduits 32 and exhaust conduits located on the other side of the cylinder head, and are for example provided with a temperature-insulating sleeve, as described below.

Figure 4:
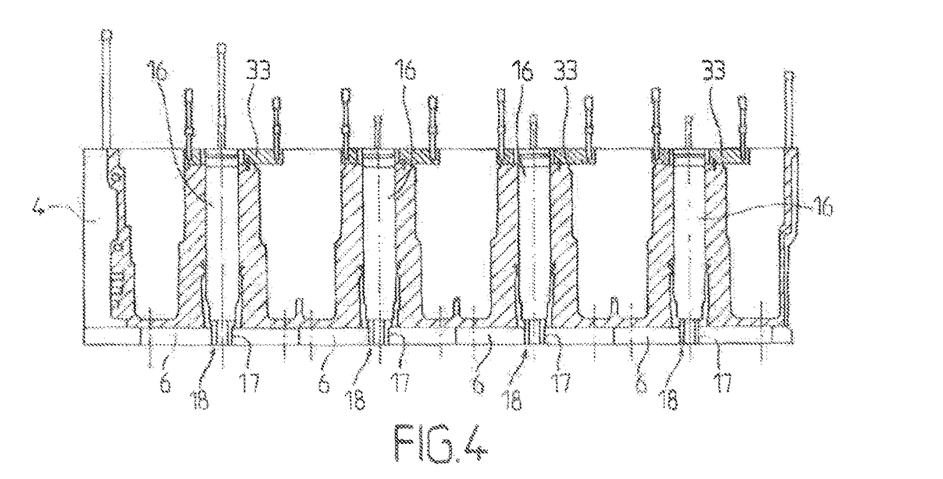
FIG. 4 is a cross section taken along the line IV-IV in FIG. 1.

FIG. 4 is a cross section taken along the line Iv-Iv in FIG. 1 showing the fastening parts 16, which are bushings designed to receive the injectors in the case of the diesel engine described in greater detail here.

These bushings bear against or are screwed on one side to a ring 33 bearing against the cylinder head body, as described below in greater detail with reference to FIG. 5.

Fastening the other side of these bushings, which are designed to receive the fuel injection injectors at the center of the combustion chambers via the central orifice 18 in the plates formed by the base plates 6, makes it possible to absorb the stresses related to the pressure in the chambers, thereby preventing bulging of each base plate element and achieving better efficiency than in the prior art (for equal cylinder head weights).

In the embodiment described, the base plate elements 6 as four semi-cylindrical notches 34 distributed symmetrically about a longitudinal plane passing through the axis 2. The notches 34 of the two respective elements 6 face one another to form a passage for the studs 27 used to fasten the cylinder head body 4 to the engine block (not shown) through the base plate elements 6.

These have a thickness e calculated to withstand the pressure and temperature stresses in the combustion chambers while enabling optimized efficient cooling by the internal cooling circuit. The thickness e is therefore for example between 2 cm and 5 cm for example 3 cm.

Figure 5:
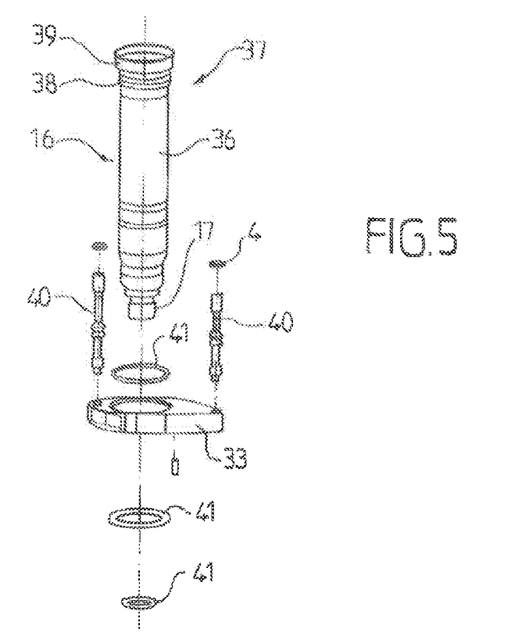
FIG. 5 is an exploded perspective view of an injector bushing and of the supporting parts of same, that can be used as a fastening part with the base plate element in FIG. 2.

FIG. 5 shows the part 16 formed by an injector bushing and the assembly elements 35 of same including the ring 33. The bushing is formed by a cylindrical body 36 for example made of a metal alloy such as the material known to the person skilled in the art by reference 40CDV20, arranged to cooperate by slip fitting inside a corresponding hole in the cylinder head body. The body 36 includes an upper extremity 37 with a two-sided part 38 and a projecting flange 39 bearing against the removable ring 33, this latter itself being arranged to bear into a recess formed for this purpose in the upper face of the cylinder head body (not shown in FIG. 5).

The ring 33 is for example formed by a plate with an orifice designed to receive by slip fitting the body that is eccentric to the plate and therefore indexable in relation to the cylinder head. The plate is fastened to the cylinder head by screws 40.

The body 36 has a lower end 17 of the fastening part 16 that is threaded and designed to be screwed into the corresponding transverse orifice 18 described above.

O-ring sealing joints 41 are provided in a known manner in the necessary places, as identified by the person skilled in the art.

Figure 6:
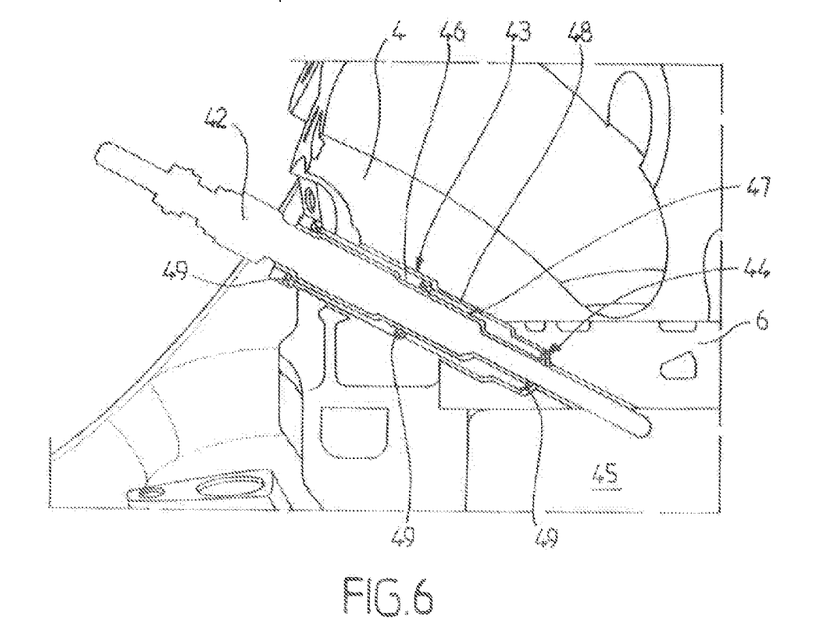
FIG. 6 is a partial cross section taken along the line VI-VI in FIG. 1 showing installation of a combustion-chamber pressure sensor.

FIG. 6 shows a partial cross section of the installation of a pressure sensor 42 or any other functional device such as a temperature sensor, injector, spark plug or gas sampling device. The sensor 42 is installed via a substantially cylindrical access duct 43 formed in the cylinder head body 4 and extended by an oblique orifice 44 made in the base plate element 6 forming a partition with the combustion chamber 45.

The access duct 43 and the oblique orifice 44 are arranged to form an empty space 46 between the outer surface 47 of the sensor 42 and the internal wall 48 of same to provide thermal insulation between the sensor, the cylinder head and the base plate.

Sealing gaskets 49 are then provided in a known manner.

Figure 7:
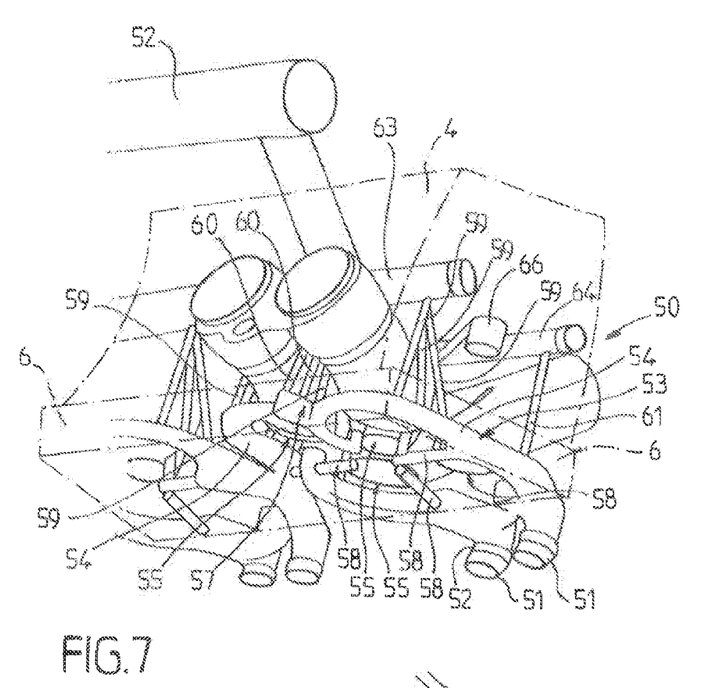
FIG. 7 is a schematic perspective three-dimensional top view of a portion of the coolant fluid circuit of the cylinder head and of the base plate described with reference to FIGS. 1 to 4 (passing notably about the supply and exhaust conduits of a chamber).
Figure 8:
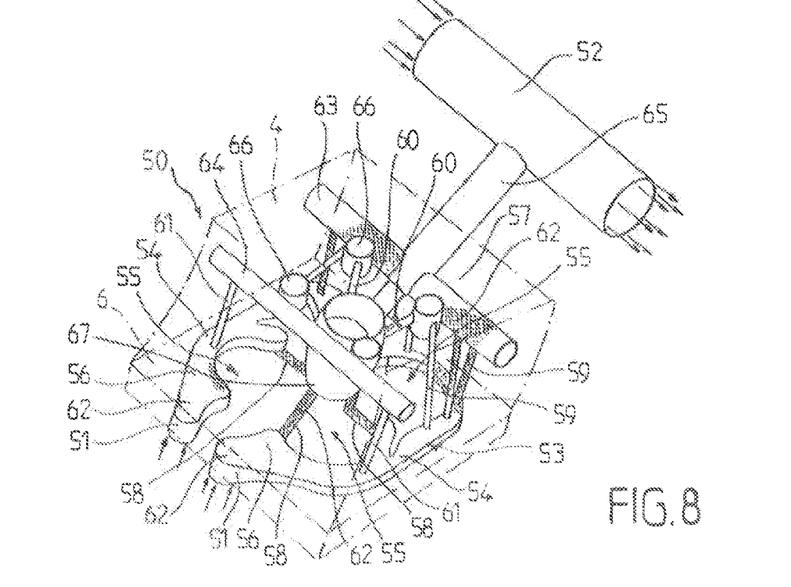
FIG. 8 is another perspective three-dimensional top view of FIG. 7 showing the hot spots.

FIGS. 7 and 8 show the internal cooling circuit 50 for the base plate elements 6 and the cylinder head body 4 (shown schematically using a mixed line), implemented according to the embodiment described in greater detail here.

The circuit 50 includes two water inlets 51 formed by circular through openings arranged symmetrically about the transverse plane of the base plate element 6. The water inlets provide fluids to the base plate and the related cylinder head, and communicate with a global coolant fluid distribution circuit 52 of the engine.

The two water inlets 51 are located at each end of the channel 53 shown in three dimensions in the FIGURES. This channel is substantially symmetrical about the transverse plane, but maybe different near to the fluid inlets as a function of thermal distributions and calculations.

More specifically, the channel 53 includes two horizontal branches 54 that turn about the valve openings 55, starting with a bean-shaped island 56 opening upwards, then form a squashed U-shape on the bottom 57 of same.

The channel thus defines a path with an average width l corresponding to the average of the distances between the inner and outer walls of the channel, the depth of which is determined to enable the cooling flow rates to achieve the speeds required to discharge the calories needed for effective cooling.

As shown above, the channel also has narrowings at the places that generate most heat, in order to cause local acceleration that improves cooling. The depth of the channel, and not just the width of same, may also be adjusted in a similar manner.

The channel 53 also has conduits 58 radiating from the central zone of the base plate elements 6, which have a diameter of between 1 cm and 0.2 mm, for example.

These conduits passed through the thickness of the space between two contiguous valves seats before opening out orthogonally on the upper face 7 of the base plate element 6.

The opening is located close to the first fastening part opening.

The conduits are bored and/or machined from the mass of the base plate.

The cooling circuit 53 also has ducts 59 (for example three) that are substantially perpendicular or form an angle of around 70° with the plane of the base plate, coming from the branches 54 and forming a curtain along one (outer) side of the exhaust ducts (not shown) in particular to cool same.

Inner ducts (between the exhausts) are also provided, such as a duct 61 dedicated to the admission ducts, which are naturally less hot.

The dimensions and number of these ducts in the cylinder head body are calculated in a known manner by the engine technician.

The grey zones 62 show the zones of the internal circuit that are particularly hot and that are handled accordingly.

The ducts 58 radiating from a central zone of the base plate include an injector bushing end, this latter being therefore highly cooled.

Once the base plate element and the adjacent zones of the cylinder head body (in particular around the gas exhaust) have been cooled, the fluid is recovered by primary manifolds 63, 64 that are higher up in the cylinder head body and that are themselves connected (link 65) to a manifold belonging to the global circuit 52, in a known manner.

Finally, a lining 66 is also provided for the valve guides and a lining or sleeve 67 is provided for the injector bushing, which are also connected to the manifolds and potentially interposed between the ducts and the manifolds.

Figure 9:
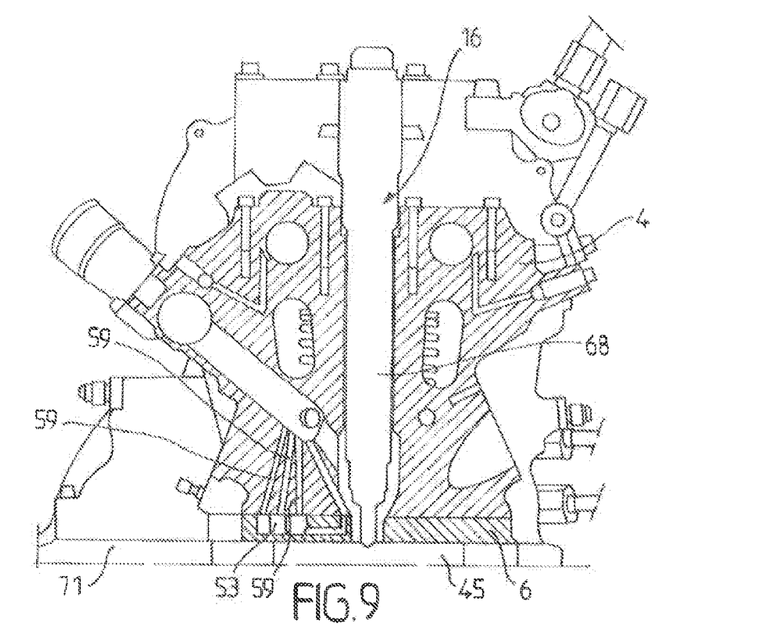
FIGS. 9 and 10 are two cross sections taken along lines IX-IX and X-X of an assembly including the engine cylinder head in FIG. 1 around the injector and the valves respectively.
Figure 10:
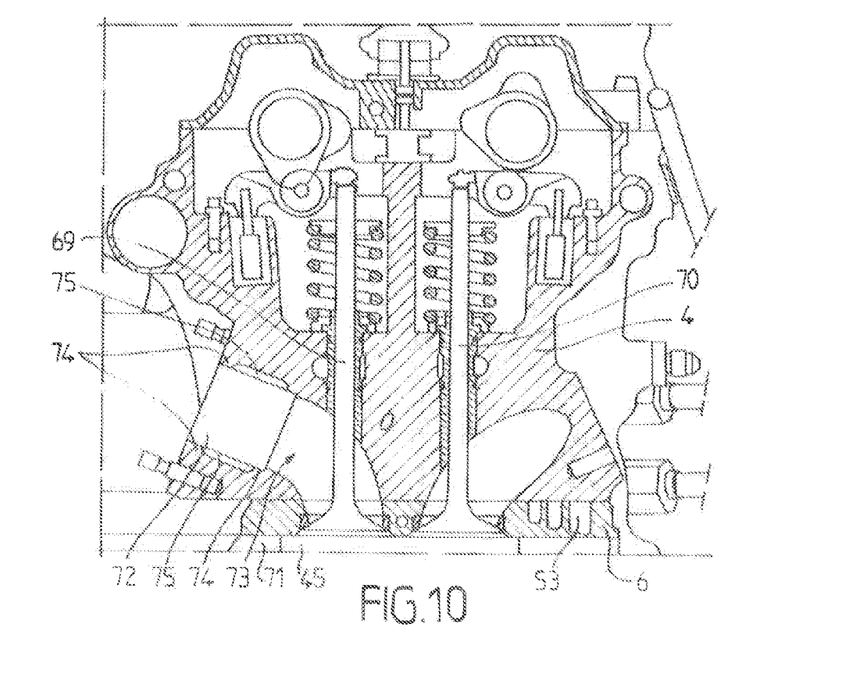

FIGS. 9 and 10 show an assembly according to the embodiment described in greater detail here, with the cylinder head body 4 shown in cross section at the fastening part 16 with an injector 68 and at an exhaust valve 69 (and an admission valve 70) respectively. The cylinder head 4 and the base plate 6 are attached to the engine block 71 and an insulating sleeve 72 is provided for the gas exhaust conduit 73 in this case.

The sleeve is for example made of a material with very low thermal conductivity. The sleeve is fixed in position in relation to the conduit 73 by peripheral portions 74 at the end of same forming a space 75 between the sleeve and the exhaust conduit portion facing the sleeve, further limiting thermal exchanges.

Operation of the cylinder head, the base plate and the assembly is described below with reference to FIGS. 3 and 8.

Throughout the engine cycles, the combustion chamber compresses the fuel/air mix and explodes same inside the chamber. This is a source of heat, temperature and mechanical stresses transmitted to the different mechanical elements of the engine, including the base plate facing the combustion chamber, the physical characteristics of which enable same to withstand higher pressures and temperatures than engines in the prior art at equivalent or lesser weights. In particular, since the pressures reached during combustion are very high (greater than 250 bars), the plate of the base plate elements is deformed.

The substantially central bearing point formed by the injector bushing creates a point of less deformation, thereby reducing the amplitude of the deformations.

This makes the base plate or the base plate element stronger and improves the seal of the combustion cylinders.

The circulation of heat-transfer fluid as described with reference to FIG. 3 further reduces the thermal effect on the base plate and around the gas exhaust conduits.

The sleeve provided also helps to limit the transmission of temperature to the cylinder head body through the exhaust conduits.

In an embodiment, by limiting the transfer of heat to the cooling water, the sleeve helps to reduce the necessary size of the heat exchangers, such as radiators. Furthermore, the materials used to make the cylinder head are thus kept within the temperature limits consistent with a range of optimum mechanical characteristics.

Furthermore, the use of a sleeve helps to keep the heat in the exhaust gases, which improves the efficiency of turbocharged engines.

This results in excellent engine efficiency, regardless of cycle, where the engines are fitted with a cylinder head according to the disclosure.

Naturally, and in consideration of the foregoing, the present disclosure is not limited to the embodiments described in greater detail. Indeed, the disclosure encompasses all variants, in particular variants in which there are more peripheral fastening screws and/or variance in which the base plate is a single part and has one or more fastening parts, regardless of the size of the engine.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A longitudinal piston-engine cylinder head, comprising:
a cylinder head body and a base plate, the base plate comprising at least one element that extends entirely within a plane, the base plate being interposed between a combustion chamber and the cylinder head body,
wherein the base plate comprising an upper face facing the cylinder head body and an opposing lower face arranged to face the combustion chamber, the base plate being attached to the cylinder head body, the cylinder head body being made of a material with mass density and hardness values that are lower than the mass density and hardness values of a material used to make the base plate,
wherein the base plate and the cylinder head body are assembled with screws used to fasten the base plate to the cylinder head body that are located towards the periphery of the base plate and of the cylinder head body and at least one part used to fasten the cylinder head body to the base plate comprising a threaded end engaged in a corresponding orifice of the base plate, said corresponding orifice being located closer to a center of the base plate than the screws,
wherein the base plate or each of at least one element of the base plate includes an internal cooling circuit to circulate a heat-transfer fluid, said internal cooling circuit having at least one fluid inlet, a fluid circulation channel and several fluid drainage channels, the several fluid drainage channels forming an angle greater than 20° with the plane of the base plate passing around gas exhaust ducts of the cylinder head body and wherein the fluid circulation channel, extending along a path, has an average width that is less than 20% of a transverse dimension of the base plate and includes, along said path, at least one narrowing of the path extending over at least 2.5% of a length of the path and an average width of at least one narrowing of the path parallel to the plane of the base plate is less than 10% of a width of the base plate.

2. The cylinder head of claim 1, wherein the cylinder head body is made of a material that has higher thermal conductivity than the material used to make the base plate.

3. The cylinder of claim 1, wherein the cylinder head body is made of aluminum, aluminum alloy, magnesium or magnesium alloy, and the base plate is made of steel or nickel alloy.

4. The cylinder head of claim 1, wherein the corresponding orifice is located within or substantially within a longitudinal plane centered on and orthogonal to the base plate.

5. The cylinder head of claim 1, wherein the base plate comprises at least two identical juxtaposed coplanar elements, each having four screws and one corresponding orifice.

6. The cylinder head of claim 4, wherein the corresponding orifice is centered in relation to the base plate and/or the at least one element of the base plate.

7. The cylinder head of claim 1, wherein the corresponding orifice passes through the base plate, and the at least one part includes a bushing arranged to individually receive a first functional device that is used in operation of an engine and that is required to interact with the combustion chamber, chosen among fuel injectors, spark plugs or ignition devices mounted in the bushings.

8. The cylinder head of claim 1, wherein the at least one part for a cylinder head passes through through-holes in the cylinder head body, bears against the cylinder head body and is screwed into the base plate, and the screws for the base plate bear against the base plate and are screwed into the cylinder head body.

9. The cylinder head of claim 1, wherein the tightening force of the at least one part is at least twice as great as the tightening force of the screws for the base plate.

10. The cylinder head of claim 1, wherein the base plate has at least one valve seat that is integral with the base plate.

11. The cylinder head of claim 1, wherein the internal cooling circuit inside the base plate has holes between at least two valve seats.

12. The cylinder head of claim 1, wherein the cylinder head has at least one sealing gasket between the cylinder head body and the base plate.

13. The cylinder head of claim 1, wherein the cylinder head body includes admission and exhaust conduits, the exhaust conduit being provided with a sleeve having a thermal conductivity of less than $70.m^{-1}.K^{-1}$, said sleeve being locked in position in relation to the exhaust conduit by end portions, away from which there is a space between said sleeve and portion of the exhaust conduit facing the sleeve, so as to limit heat exchange.

14. The cylinder head of claim 1, wherein the base plate includes an opening for a second functional device that is used in operation of an engine and that is required to interact with the combustion chamber chosen among fuel injectors, spark plugs or ignition devices mounted in the bushings.

15. An element of a base plate for a cylinder head of a piston engine, the element extending entirely within a plane, having an upper face and an opposing lower face and being designed to be interposed as an interface between a combustion chamber of the engine and a cylinder head body,
the upper face having an internal cooling circuit to circulate a heat-transfer fluid,
wherein said element is designed to be coplanar with other identical elements that form the base plate, and wherein said internal cooling circuit having at least one fluid inlet, a fluid circulation channel and several fluid drainage channels, the several fluid drainage channels forming an angle greater than 20° with the plane of the element passing around a gas exhaust duct of the cylinder head body and wherein the fluid circulation channel, extending along a path, has an average width that is less than 20% of a transverse dimension of the base plate and includes, along said path, at least one narrowing of the path extending over at least 2.5% of a length of the path and an average width of at least one narrowing of the path parallel to the plane of the base plate is less than 10% of a width of the base plate
the element further comprising:
first through-holes for screws for fastening the element to the cylinder head body that are located towards the periphery of the element; and
at least one second screw orifice for a part for fastening the cylinder head body to said element that is closer to the center of the base plate than the first fastening holes through-holes.

16. A base plate for a cylinder head of a piston engine, the base plate being elongated in a direction extending entirely within a plane, having an upper face and an opposing lower face and being designed to be interposed as an interface element between a combustion chamber of the piston engine and a cylinder head body, wherein the base plate comprises:
an internal cooling circuit to circulate a heat-transfer fluid, said internal cooling circuit having at least one fluid inlet, a fluid circulation channel and several fluid drainage channels, the several fluid drainage channels forming an angle greater than 20° with the plane of the base plate passing around gas exhaust ducts of the cylinder head body and wherein the fluid circulation channel, extending along a path, has an average width that is less than 20% of a transverse dimension of the base plate and includes, along said path, at least one narrowing of the path extending over at least 2.5% of a length of the path and an average width of at least one narrowing of the path parallel to the plane of the base plate is less than 10% of a width of the base plate.

* * * * *